United States Patent [19]

Kemp

[11] 4,356,122
[45] Oct. 26, 1982

[54] 6-PERHALOALKYLSULFONYLOXY-PENICILLANIC ACIDS AND DERIVATIVES THEREOF

[75] Inventor: John E. G. Kemp, Canterbury, England

[73] Assignee: Pfizer Inc., New York, N.Y.

[21] Appl. No.: 214,846

[22] Filed: Dec. 10, 1980

Related U.S. Application Data

[63] Continuation-in-part of Ser. No. 147,438, May 7, 1980, abandoned.

[30] Foreign Application Priority Data

May 19, 1979 [GB] United Kingdom ................ 7917505

[51] Int. Cl.³ ............................................ C07D 499/00
[52] U.S. Cl. .............................. 260/245.2 R; 424/270
[58] Field of Search ................. 260/245.2 R; 424/270

[56] References Cited

U.S. PATENT DOCUMENTS 4,143,046  3/1979  Sheehan ........................... 260/306.7
4,265,882  5/1981  Sheehan et al. .............. 260/245.2 R
4,282,149  8/1981  Sheehan et al. .............. 260/245.2 R

OTHER PUBLICATIONS

Hauser et al., Helv. Chim. Acta, 50, 1327 (1967).
Sheehan et al., J. Org. Chem. 42, 2224 (1977).

*Primary Examiner*—Nicholas S. Rizzo
*Attorney, Agent, or Firm*—Charles J. Knuth; Albert E. Frost; Peter C. Richardson

[57] ABSTRACT

6-Alpha and 6-beta-substituted penicillanic acid derivatives of the formula:

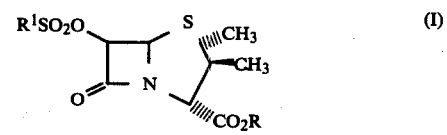

wherein R is H or a conventional penicillin carboxy protecting group or an ester forming residue readily hydrolyzable in vivo and $R^1$ is a perhaloalkyl group of from 1 to 4 carbon atoms wherein the halogen atoms are fluoro or chloro, undergo $SN_2$ nucleophilic displacement with halide or azide ions with inversion of configuration at C-6 to yield the corresponding 6-beta or 6-alpha-halo- or azido-substituted product.

6 Claims, No Drawings

6-PERHALOALKYLSULFONYLOXY-PENICILLANIC ACIDS AND DERIVATIVES THEREOF

CROSS-REFERENCE TO RELATED APPLICATION

This application is a continuation-in-part of U.S. patent application Ser. No. 147,438, filed May 7, 1980, now abandoned.

BACKGROUND OF THE INVENTION

This invention relates to penicillins and in particular to novel 6-perhaloalkylsulfonyloxypenicillanic acid derivatives which are valuable intermediates in the preparation of biologically active 6-substituted penicillanic acids.

A number of 6-beta-substituted penicillanic acid derivatives are of interest as antibiotics and as beta-lactamase inhibitors. For example, U.S. patent application Ser. No. 17,809, filed Mar. 5, 1979, now abandoned, and U.S. patent application Ser. No. 96,832, filed Nov. 23, 1979 disclose 6-beta-halo-penicillanic acids and biolabile esters thereof as potent beta-lactamase inhibitors.

U.S. patent application Ser. No. 86,864, filed Oct. 22, 1979 now U.S. Pat. No. 4,287,181 by M. S. Kellogg, entitled "Derivatives of 6β-Hydroxyalkylpenicillanic Acids as β-Lactamase Inhibitors" describes 6-beta-alkylsulfonyloxyalkyl-6-beta-phenylsulfonyloxyalkyl- and 6-beta-(substituted phenyl)sulfonyloxyalkylpenicillanic acids as beta-lactamase inhibitors.

SUMMARY OF THE INVENTION

We have discovered that 6-alpha-perhaloalkylsulfonyloxypenicillanic acid esters undergo nucleophilic substitution at C-6 to yield the 6-beta-substituted derivative. Such SN$_2$ displacements at C-6 on penicillanic acid have evaded the efforts of chemists for more than a decade, the closest precedents being the preparation of a very limited range of 6-substituted compounds via 6-diazopenicillanic acid. Such compounds are therefore valuable intermediates in the preparation of a variety of 6-beta-substituted penicillanic acid derivatives referred to above. The corresponding 6-beta-perhaloalkylsulfonyloxypenicillanic acids may also be used to yield 6-alpha-substituted penicillanic acid derivatives.

Thus, according to the invention there are provided 6-alpha- and 6-beta-substituted penicillanic acid derivatives of the formula:

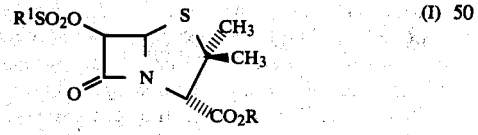

where R is H or a conventional penicillin carboxy protecting group or an ester forming residue readily hydrolyzable in vivo; and $R^1$ is a perfluoroalkyl or perchloroalkyl group having from 1 to 4 carbon atoms.

By the term "ester forming residue readily hydrolyzable in vivo" is meant a non-toxic ester group which is rapidly cleaved upon administration to an animal or human being, either in the stomach, the blood or the tissues to give the free acid. Examples of such R groups are well-known and are readily identified by those skilled in the art, they include: lower alkanoyloxymethyl, 1-(lower alkanoyloxy)ethyl, 1-methyl-1-(lower alkanoyloxy)ethyl, lower alkoxycarbonyloxymethyl, 1-(lower alkoxycarbonyloxy)ethyl and 1-methyl-1-(lower alkoxycarbonyloxy)ethyl groups. Particular examples are the pivaloyloxymethyl, acetoxymethyl, 1-ethoxycarbonyloxyethyl, 3-phthalidyl, 4-crotonolactonyl and gamma-butyrolacton-4-yl groups.

Conventional penicillin carboxy protecting groups include such groups as are known to be of value in the art for protecting the carboxy group in penicillins and which may be introduced and removed under mild conditions without affecting the penicillin nucleus. Typical carboxy protecting groups are benzyl and substituted benzyl (e.g. p-methoxybenzyl and p-nitrobenzyl), benzhydryl, trimethylsilyl, tetrahydropyranyl, trichloroethyl, phenacyl and trimethylsilylethyl.

The perfluoroalkyl and perchloroalkyl groups are referred to herein as perhaloalkyl groups. Representative of such groups are the trifluoromethyl, trichloromethyl and the nonafluorobutyl group; the trifluoromethyl and nonafluorobutyl groups being generally preferred.

The term "lower" as applied to an alkyl, alkoxy or alkanoyl group herein means that the group contains up to six carbon atoms. Such groups may be straight or branched chain.

In the formulae a broken line indicates that the substituent is below the plane of the bicyclic nucleus. Such a substituent is said to be in the alpha-configuration. Conversely wedge attachment of a substituent indicates that it is above the plane of the nucleus and is in the beta-configuration.

DETAILED DESCRIPTION OF THE INVENTION

The 6-alpha- and 6-beta-perhaloalkylsulfonyloxypenicillanic acid derivatives of the formula (I) may be prepared from a 6-hydroxypenicillanic acid or ester of the formula:

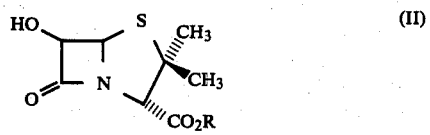

wherein R is as previously defined by reaction with a perhaloalkylsulfonyl halide or anhydride and optionally, if desired, removing the carboxy protecting group to obtain those compounds where R is hydrogen, and optionally protecting the compound of the formula (II) wherein R is hydrogen with a conventional penicillin carboxy protecting group.

The reaction is generally performed by adding the sulfonyl halide or anhydride to a solution of the compound of formula (II) in a reaction-inert organic solvent, e.g. chloroform or ethyl acetate. A slight excess e.g. a 10% excess, of the sulfonyl halide or anhydride is generally used and it is conveniently added as a solution in the same solvent as used for the compound of formula (II). Trifluoromethane sulfonyl chloride is a preferred sulfonyl halide. An organic base, e.g. triethylamine, is added with advantage to assist the reaction and to neutralize the liberated acid. The reaction may be performed at a temperature of from −20° C. to the reflux temperature of the solvent but it is preferably performed with cooling at 0° C. to avoid the formation of by-products. The reaction is generally complete after 15 to 30 minutes under these conditions and the product is then worked up in a conventional manner, e.g. by dilution with water, solvent extraction and evaporation of the solvent. The product may be further purified if desired by conventional methods, e.g. by column chromatography on silica.

Removal of the ester protecting group from the product to give the compounds of formula (I) wherein R is hydrogen is achieved using methods appropriate to the particular protecting group employed and such methods and conditions for their performance will be well known to those skilled in the art.

The medium employed may be anhydrous or aqueous and in particular instances it may be acidic or basic to various strengths. Thus in the case where R is a 2,2,2-trichloroethyl group it may be removed by treating with zinc in acetic acid or, when R is 4-methoxybenzyl, it may be removed by reaction with trifluoroacetic acid. In either case the free acid is isolated and further purified, if desired, using conventional techniques e.g. by column chromatography on silica.

The free acid may also be further esterified, if desired. For example, the trimethylsilyl ester may be prepared by reaction of the free acid with a trimethylsilylating reagent, e.g. bis(trimethylsilyl)acetamide, and the product may be isolated or reacted in situ as hereinafter described to give 6-substituted derivatives.

The compounds of formula (II) are in some cases known compounds or they may be prepared by analogous methods. Thus J. C. Sheehan et al., *J. Org. Chem.*, 1974, 39, 1444 describes the preparation of a number of esters of 6-alpha-hydroxypenicillanic acid including the benzhydryl ester (although this compound is incorrectly referred to as the 6-beta-hydroxy ester). The compounds of formula (II) where R is an ester or carboxy protecting group may also be prepared by conventional esterification procedures using the known 6-alpha-hydroxypenicillanic acid (D. Hauser and H. P. Sigg, *Helv. Chim. Acta*, 1967, 50, 1327).

The 6-beta-perhaloalkylsulfonyloxypenicillanic acid derivatives may be prepared in an exactly analogous manner but naturally starting with the corresponding 6-beta-hydroxypenicillanic acid or ester. Esters of 6-beta-hydroxypenicillanic acid are again known in some cases or they may be prepared by analogous methods. For example, 6-beta-hydroxypenicillanic acid pivaloyloxymethyl ester may be prepared from the known 6-aminopenicillanic acid ester (W. V. Daehne et al., *J. Med. Chem.*, 1970, 13, 607) by diazotization followed by reaction with triphenylphosphine and nitrous acid to give the 6-oxo-penicillanate which is reduced with sodium borohydride. Similarly, 6-beta-hydroxypenicillanic acid 2,2,2-trichloroethyl ester may be obtained by sodium borohydride reduction of the known 6-oxo ester (J. C. Sheehan et al., *J. Org. Chem.*, 1977, 42, 4045).

The compounds of formula (I) undergo displacement reactions with a variety of nucleophiles to yield 6-substituted penicillanic acid derivative with inversion of configuration at C-6. Suitable nucleophiles include, for example, halide ion, and azide ion.

One particularly valuable process according to this aspect of the invention is the displacement of a 6-alpha-perhaloalkylsulfonyloxy derivative of formula (I) with iodide, chloride, bromide or azide ion to yield the corresponding 6-beta-substituted derivative.

Thus the invention also provides a process for the preparation of 6-beta-substituted penicillanic acid derivatives of the formula:

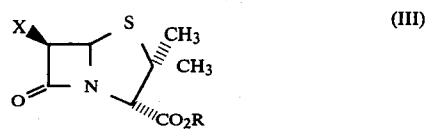

wherein X is bromo, chloro, iodo or azido and $R^2$ is hydrogen or an ester forming residue readily hydrolyzable in vivo which comprises reacting a 6-alpha-substituted compound of the formula (I) with a metal bromide, chloride, iodide, or azide, and, in the case where R is a carboxy protecting group, removing the protecting group and isolating the compound of formula (III).

The 6-substituted compounds of formula III are known antibacterial agents and/or intermediates.

The process is generally performed with the compound of the formula (I) dissolved in a reaction-inert organic solvent, e.g. acetone, tetrahydrofuran, or N,N-dimethylformamide, and the metal halide or azide, e.g. sodium iodide, is added in excess. The reaction mixture is conveniently stirred at room temperature for a day or two and when the reaction is substantially complete (as indicated by thin-layer chromatography) the reaction mixture may be worked-up in a conventional manner, e.g. by dilution with water, solvent extraction and evaporation of the solvent. The product may be further purified if desired, particularly if a compound of formula (I) wherein R is ester forming residue readily hydrolyzable in vivo is used, to give a compound of the formula (III) wherein $R^2$ is the same ester forming residue readily hydrolyzable in vivo as the desired product; otherwise the product may be used directly in the next stage of the reaction.

Removal of the ester protecting group from the product derived from reaction of a compound of the formula (I) wherein R is a conventional penicillin carboxy protecting group, is achieved using methods appropriate to the particular protecting group as previously described. Particularly preferred protecting groups for the compound of formula (I) are the benzhydryl and 4-methoxy benzyl groups, which may be removed under acidic conditions, e.g. using trifluoroacetic acid. Thus in these cases the product from the first stage of the process, following reaction with the metal halide or azide, is dissolved in reaction-inert organic solvent, e.g. dichloromethane, and trifluoroacetic acid added. A period of 30 minutes at room temperature is usually sufficient to ensure complete deprotection and the product is then generally isolated by removal of the solvents and may be further purified if desired using conventional techniques, e.g. by column chromatography on silica.

Further preferred protecting groups for this process are the trimethylsilyl ester which is removed by contact with water and is thus generally lost during the aqueous work-up without the need for a separate deprotection step, and the 4-nitrobenzyl ester which is removed by treatment with sodium dithionite.

A particularly valuable process according to this aspect of the invention is the process for preparing the compound of formula (III) wherein X is iodo and $R^2$ is hydrogen. The reaction of a compound of formula (I) wherein $R^1$ is trifluoromethylsulfonyl and R is benzhydryl, 4-methoxybenzyl, 4-nitrobenzyl or trimethylsilyl with a metal iodide is particularly useful in this regard.

This invention is illustrated by the following examples in which Examples 1 to 7, 15 and 16 are examples of the preparation of the novel compounds of formula (I), and Examples 8 to 14 are examples of their use in the process for the preparation of compounds of the formula (III). Preparation of certain starting materials of formula (II) are given in Preparations 1 to 5.

EXAMPLE 1

6-alpha-Trifluoromethylsulfonyloxypenicillanic Acid Benzhydryl Ester

A solution of trifluoromethane sulfonyl chloride (190 mg.) in chloroform (2 ml.) was added to a mixture of 6-alpha-hydroxypenicillanic acid benzhydryl ester (383 mg.) and triethylamine (125 mg.) in chloroform (13 ml.) at 0° C. and the resulting mixture was stirred for 30 minutes. The solution was poured onto crushed ice (10 g.) and extracted repeatedly with chloroform. The combined chloroform extracts were washed with water, dried (MgSO$_4$) and the solvent evaporated to yield a pale yellow gum which was chromatographed over silica eluting with a 1:9 mixture of ethyl acetate and petroleum ether (b.p. 60°–80° C.). Evaporation of the relevant fractions gave 6-alpha-trifluoromethylsulfonyloxypenicillanic acid benzhydryl ester (422 mg., 82%), as a pale yellow gum.

N.M.R. (CDCl$_3$) delta: 1.25 (s, 3H); 1.53 (s, 3H); 4.65 (s, 1H); 5.53 (2H); 7.00 (s, 1H); 7.40 (s, 10H).

I.R.: 1795, 1740 cm$^{-1}$.

T.L.C. (silica/ethyl acetate): R$_f$ 0.8.

EXAMPLE 2

6-alpha-Trifluoromethylsulfonyloxypenicillanic Acid 4-methoxybenzyl Ester

A solution of trifluoromethane sulfonyl chloride (0.70 g.) in chloroform (2 ml.) was added dropwise to a stirred ice-cold solution of 6-alpha-hydroxypenicillanic acid 4-methoxybenzyl ester (0.93 g.) and triethylamine (0.55 g.) in chloroform (50 ml.). After 15 minutes the solution was washed with water (50 ml.), dried (MgSO$_4$) and evaporated to dryness. The product was chromatographed on silica eluting with pentane containing an increasing proportion of dichloromethane.

Evaporation of the relevant fractions gave 6-alpha-trifluoromethylsulfonyloxypenicillanic acid 4-methoxybenzyl ester (0.70 g.), m.p. 69°–71° C.

Analysis %: Found: C, 43.59; H, 3.81; N, 2.62. C$_{17}$H$_{18}$NO$_7$SF$_3$ requires: C, 43.50; H, 3.84; N, 2.99.

N.M.R. (CDCl$_3$) delta: 1.36 (s, 3H); 1.53 (s, 3H); 3.80 (s, 3H); 4.52 (s, 1H); 5.12 (s, 2H); 5.48 (2H); 7.08 (q, 4H).

T.L.C. (silica/dichloromethane): R$_f$ 0.3.

EXAMPLE 3

6-beta-Trifluoromethylsulfonyloxypenicillanic Acid 2,2,2-Trichloroethyl Ester 2,2,2-Trichloroethyl 6-beta-hydroxypenicillanate (0.24 g.) in dichloromethane (10 ml.) was cooled to 0° C. and stirred while trifluoromethanesulfonyl chloride (0.16 g.) followed by triethylamine (0.085 g.) in dichloromethane (1 ml.) were added dropwise. Stirring at 0° C. was continued for a further 1¼ hours and the solution was then washed with water, dried (MgSO$_4$) and the solvent evaporated to yield 6-beta-trifluoromethylsulfonyloxypenicillanic acid 2,2,2-trichloroethyl ester (0.29 g.) as a pale yellow oil.

N.M.R. (CDCl$_3$) delta: 1.62 (s, 3H); 1.75 (s, 3H); 4.74 (s, 1H); 5.70 (d, 1H, J=4.0 Hz); 5.94 (d, 1H, J=4.0 Hz).

I.R. (film): 1815, 1760 cm$^{-1}$.

EXAMPLE 4

6-beta-Trifluoromethylsulfonyloxypenicillanic Acid Pivaloyloxymethyl Ester

This compound was prepared by the general method of Example 3 but starting with pivaloyloxymethyl 6-beta-hydroxypenicillanate.

N.M.R. (CDCl$_3$) delta: 1.22 (s, 9H); 1.48 (s, 3H); 1.60 (s, 3H); 5.65 (d, 1H, J=4.0 Hz) and 5.90 (d, 1H, J=4.0 Hz); 5.85 (AB system, 2H).

I.R. (film): 1815, 1770 cm$^{-1}$.

EXAMPLE 5

6-beta-Trifluoromethylsulfonyloxypenicillanic Acid 2,2,2-Trichloroethyl 6-beta-trifluoromethanesulfonylpenicillanate (200 mg.) was dissolved in aqueous 90% acetic acid, and activated zinc (65 mg.) was added. The mixture was stirred at room temperature for 1 hour, then more zinc (30 mg.) was added and the mixture stirred for a further 1 hour. The mixture was filtered, the filtrate was evaporated to dryness, the residue was extracted with ethyl acetate and the solvent evaporated. The resulting crude product was purified by preparative t.l.c. on silica eluting with 5% acetic acid in ethyl acetate to give 6-beta-trifluoromethylsulfonyloxypenicillanic acid (23 mg.).

N.M.R. (CDCl$_3$) delta: 1.61 (s, 3H); 1.70 (s, 3H); 4.60 (s, 1H); 5.64 (d, J=4.0 Hz, 1H); 5.91 (d, J=4.0 Hz, 1H).

I.R. (film): 1815 cm$^{-1}$ (beta-lactam carbonyl).

EXAMPLE 6

6-alpha-Trifluoromethylsulfonyloxypenicillanic Acid

4-Methoxybenzyl 6-alpha-trifluoromethylsulfonyloxypenicillanate (100 mg.) was dissolved in trifluoroacetic acid (1 ml.) and after 15 seconds evaporated to dryness. Column chromatography of the residue on silica eluting with petrol containing increasing amounts of ethyl acetate yielded 62 mg. impure product, which was triturated with diisopropyl ether and purified by preparative t.l.c. on silica with 5% acetic acid in ethyl acetate to give pure 6-alpha-trifluoromethylsulfonyloxypenicillanic acid (17 mg.).

T.L.C.: R$_f$ 0.45 (5% acetic acid/ethyl acetate on SiO$_2$).

N.M.R. (CDCl$_3$) delta: 1.57 (s, 3H); 1.61 (s, 3H); 4.56 (s, 1H); 5.51 (s, 2H); 9.07 (bs, HO group).

I.R. (film): 1815 cm$^{-1}$ (beta-lactam carbonyl).

EXAMPLE 7

6-alpha-Nonafluorobutylsulfonyloxypenicillanic Acid Benzhydryl Ester

Benzhydryl 6-alpha-hydroxypenicillanate (1.91 g.) in chloroform (19 ml.) was treated successively with triethylamine (505 mg.) and nonafluorobutylsulfonyl fluoride (1.5 g.). The reaction was complete after 20 minutes and was worked up by evaporation of the solvent and chromatography on silica, eluting with petrol containing increasing amounts of methylene chloride, to give 6-alpha-nonafluorobutylsulfonyloxypenicillanic acid benzhydryl ester (1.8 g.), m.p. 74°–76° C.

Analysis %: Found: C, 45.04; H, 2.82; N, 2.20. C$_{25}$H$_{19}$F$_9$NO$_6$S requires: C, 45.11; H, 3.00; N, 2.11.

N.M.R. (CDCl$_3$) delta: 1.36 (s, 3H); 1.65 (s, 3H); 4.69 (s, 1H); 5.58 (bs, 2H); 6.99 (s, 1H); 7.37 (bs, 10H).

I.R. (KBr): 1793 cm$^{-1}$ (beta-lactam carbonyl); 1738 cm$^{-1}$ (ester carbonyl).

EXAMPLE 8

6-beta-Iodopenicillanic Acid (A) A mixture of 6-alpha-trifluoromethylsulfonyloxypenicillanic acid 4-methoxybenzyl ester (5 g.), sodium iodide (12.5 g.) and acetone (100 ml.) was stirred at room temperature for 46 hours. The resulting mixture was concentrated to 10 ml., diluted with water (200 ml.) and extracted with ether (200 ml.). The ether extract was dried over $MgSO_4$ and evaporated to yield 6-beta-iodopenicillanic acid 4-methoxybenzyl ester as an oil (4.8 g.).

(B) Trifluoroacetic acid (2 ml.) was added to a solution of the product from A (0.38 g.) in dichloromethane (20 ml.). The solution was stirred at room temperature for 30 minutes and the solution was then evaporated under vacuum and the residue chromatographed on a column of silica eluting with a 1:3 mixture of ethyl acetate and petroleum ether (b.p. 60°-80° C.). The relevant fractions containing the product were combined and evaporated to a low volume. The crystalline precipitate was collected by filtration, washed with a 1:1 mixture of dichloromethane and pentane and dried to yield 6-beta-iodopenicillanic acid (27 mg.), m.p. 120° C. (dec.).

The product was spectroscopically and chromatographically identical to a reference sample.

N.M.R. ($CDCl_3$) delta: 1.57 (s, 3H); 1.74 (s, 3H); 4.57 (s, 1H+1H); 5.39 (d, 1H, J=4.0 Hz); 5.65 (d, 1H, J=4.0 Hz); 9.0 (bs, 1H).

EXAMPLE 9

6-beta-Iodopenicillanic Acid (A) The procedure of Example 8(A) was followed using 6-alpha-trifluoromethylsulfonyloxypenicillanic acid benzhydryl ester to give 6-beta-iodopenicillanic acid benzhydryl ester.

N.M.R. ($CDCl_3$) delta: 1.24 (s, 3H); 1.65 (s, 3H); 4.62 (s, 1H); 5.36 (d, 1H); 5.56 (d, 1H); 6.95 (s, 1H); 7.36 (s, 10H).

(B) 6-beta-Iodopenicillanic acid benzhydryl ester (80 mg.) was dissolved in dichloromethane (1 ml.) and trifluoroacetic acid (0.5 ml.) added. The solution was stirred at room temperature for 30 minutes and then evaporated to dryness to yield 76 mg. of product, identified by thin-layer chromatography, i.r. spectrum and n.m.r. to be 6-beta-iodopenicillanic acid contaminated with some benzhydryl-derived by-product.

EXAMPLE 10

6-beta-Bromopenicillanic Acid (A) Lithium bromide (68 mg.) was added to a solution of 6-alpha-trifluoromethylsulfonyloxypenicillanic acid benzhydryl ester (400 mg.) in N,N-dimethylformamide (3 ml.) and the mixture stirred at room temperature for 17 hours. The solvent was evaporated and the residue chromatographed on silica eluting with hexane containing increasing amounts of methylene chloride to give benzhydryl 6-beta-bromopenicillanate (73 mg.).

N.M.R. ($CDCl_3$) delta: 1.26 (s, 3H); 1.65 (s, 3H); 4.61 (s, 1H); 5.30 (d, J=4.0 Hz, 1H); 5.67 (d, J=4.0 Hz, 1H); 6.95 (s, 1H); 7.35 (bs, 10H).

I.R. (film): 1795 $cm^{-1}$ (beta-lactam carbonyl).

(B) Treatment of benzhydryl 6-beta-bromopenicillanate with trifluoroacetic acid as described in Example 9(B) gave 6-beta-bromopenicillanic acid, identical to a reference sample.

EXAMPLE 11

6-beta-Azidopenicillanic Acid (A) Lithium azide (50 mg.) was added to a solution of 6-alpha-trifluoromethylsulfonyloxypenicillanic acid 4-nitrobenzyl ester (485 mg.) in N,N-dimethylformamide (5 ml.) and the mixture kept at room temperature for a period of two weeks. The mixture was partitioned between chloroform and water, the organic phase separated and evaporated, and the residue chromatographed on silica eluting with petrol containing methylene chloride to yield 4-nitrobenzyl-6-beta-azidopenicillanate (160 mg.).

N.M.R. ($CDCl_3$) delta: 1.43 (s, 3H); 1.57 (s, 3H); 4.52 (s, 1H); 4.96 (d, J=4.0 Hz, 1H); 5.28 (s, 2H); 5.47 (d, J=4.0 Hz, 1H); 7.57 (d, J=8.5 Hz, 2H); 8.25 (d, J=8.5 Hz, 2H).

I.R. (film): 2130 $cm^{-1}$ ($N_3$); 1790 $cm^{-1}$ (beta-lactam, C=O); 1760 $cm^{-1}$ (ester).

(B) A solution of 4-nitrobenzyl 6-beta-azidopenicillanate (150 mg.) in acetonitrile (10 ml.) was treated with water (5 ml.) and sodium dithionite (150 mg.). The mixture was stirred for 15 minutes at room temperature and then partitioned between ethyl acetate and water. The aqueous phase was acidified to pH 2.5 and the organic phase separated and evaporated. The residue was chromatographed on silica eluting first with pentane and then with ethyl acetate containing 5% ethanol to yield 6-beta-azidopenicillanic acid (22 mg.) as an oil which slowly solidified on standing.

N.M.R. ($CD_3COCD_3$) delta: 1.56 (s, 3H); 1.68 (s, 3H); 4.41 (s, 1H); 5.26 (d, J=4.0 Hz, 1H); 5.55 (d, J=4.0 Hz, 1H).

I.R. (film): 2120 $cm^{-1}$ ($N_3$); 1785 $cm^{-1}$ (beta-lactam, C=O).

EXAMPLE 12

6-beta-Azidopenicillanic Acid (A) 6-alpha-Nonafluorobutylsulfonyloxypenicillanic acid benzhydryl ester (2 g.) was treated with lithium azide as described in Example 11(A) to give benzhydryl 6-beta-azidopenicillanate (0.9 g.).

N.M.R. ($CDCl_3$) delta: 1.25 (s, 3H); 1.63 (s, 3H); 4.55 (s, 1H); 4.86 (d, J=4.5 Hz, 1H); 5.44 (d, J=4.5 Hz, 1H); 6.93 (s, 1H); 7.32 (s, 10H).

I.R. (film): 2112 $cm^{-1}$ ($N_3$); 1789 $cm^{-1}$ (beta-lactam, C=O).

(B) The product from (A) is deprotected using the procedure of Example 9(B) to yield 6-beta-azidopenicillanic acid identical to the product of Example 11(B).

EXAMPLE 13

Sodium 6-beta-Iodopenicillanate (A) Bis(trimethylsilyl)acetamido (3.19 g., 157 mmoles) was added to a solution of 6-alpha-trifluoromethylsulfonyloxypenicillanic acid (5 g., 143 mmoles) in acetone (50 ml.) and the solution was stirred at 35°-40° C. for 30 minutes. Sodium iodide (2.35 g., 157 mmoles) was added to the resulting solution of 6-alpha-trifluoromethylsulfonyloxypenicillanic acid trimethylsilyl ester and the mixture was stirred at 60°-65° C. for 30 minutes. The solvent was evaporated under vacuum to yield 6-beta-iodopenicillanic acid trimethylsilyl ester as a thick red oil.

(B) The product from (A) was stirred with ethyl acetate (50 ml.) and water (50 ml.), the organic layer was separated, washed with water (2×25 ml.) and dried over anhydrous magnesium sulfate. An ethyl acetate solution of sodium 2-ethylhexanoate (3.57 g., 215 mmoles) was added to the ethyl acetate solution of the acid and the mixture stirred at room temperature for 30 minutes.

The crystalline precipitate was collected by filtration, washed with ethyl acetate and ether and dried to yield sodium 6-beta-iodopenicillanate (3.3 g., 66%) identical to a reference sample.

EXAMPLE 14

6-beta-Chloropenicillanic Acid (A) Lithium chloride (50 mg.) was added to a solution of 6-alpha-trifluoromethylsulfonyloxypenicillanic acid benzhydryl ester (550 mg.) in N,N-dimethylformamide (2 ml.) and the mixture stirred at room temperature for 17 hours. The solvent was evaporated and the residue chromatographed on silica eluting with pentane containing increasing amounts of methylene chloride to give benzhydryl 6-beta-chloropenicillanate (162 mg.), $R_f$ 0.35 ($CH_2Cl_2/SiO_2$), a white foam.

N.M.R. ($CDCl_3$) delta: 1.25 (s, 3H); 1.61 (s, 3H); 4.56 (s, 1H); 5.16 (d, J=4.0 Hz, 1H); 5.66 (d, J=4.0 Hz, 1H); 6.92 (s, 1H); 7.33 (bs, 10H).

I.R. (film): 1795 (beta-lactam carbonyl).

(B) Treatment of benzhydryl 6-beta-chloropenicillanate with trifluoroacetic acid, as described in Example 9(B) gives 6-beta-chloropenicillanic acid.

EXAMPLE 15

6-alpha-Trifluoromethylsulfonyloxypenicillanic Acid Benzhydryl Ester

Triethylamine (2.63 g.) and trifluoromethanesulfonic anhydride (8.0 g.) were added to a solution of 6-alpha-hydroxypenicillanic acid benzhydryl ester (10.0 g.) in chloroform (100 ml.) at 0° C. The reaction mixture was stirred at room temperature for 2 hours then washed with water (2×100 ml.), dried over $MgSO_4$ and evaporated to yield a dark gum. Chromatography on silica eluting with a mixture of hexane and dichloromethane gave the product (4 g.) identical to the product of Example 1.

EXAMPLE 16

6-alpha-Trifluoromethylsulfonyloxypenicillanic Acid 4-Nitrobenzyl Ester 6-alpha-Hydroxypenicillanic acid 4-nitrobenzyl ester (1.9 g.) was treated with trifluoromethane sulfonyl chloride as described in Example 2. The product was chromatographed as described in Example 2 to yield 6-alpha-trifluoromethylsulfonyloxypenicillanic acid 4-nitrobenzyl ester (1.3 g.) as a red oil.

N.M.R. ($CDCl_3$) delta: 1.38 (s, 3H); 1.53 (s, 3H); 4.58 (s, 1H); 5.20 (s, 2H); 5.48 (s, 2H); 7.45 (d, J=8 Hz, 2H); 8.16 (d, J=8 Hz, 2H).

PREPARATION 1

6-alpha-Hydroxypenicillanic Acid Benzhydryl Ester

Diphenyldiazomethane (1 g.) was added to a solution of 6-alpha-hydroxypenicillanic acid (1 g.) in a mixture of methylene chloride (13 ml.) and methanol (4 ml.). Further portions of diphenyldiazomethane were added at 4 hours (0.5 g.) and 6 hours (0.25 g.). The mixture was allowed to stand at room temperature overnight and the solvent removed under vacuum. The residue was chromatographed on silica eluting with a 1:3 mixture of ethyl acetate and petroleum ether (b.p. 60°-80° C.). Fractions containing the product were combined and evaporated to yield 6-alpha-hydroxypenicillanic acid benzhydryl ester (0.6 g.) as a yellow foam. N.M.R. and i.r. data were in agreement with literature [J. C. Sheehan, Y. S. Lo, J. Loliger and C. Podewell, J. Org. Chem., 39, 1444 (1974)] values.

PREPARATION 2

6-alpha-Hydroxypenicillanic Acid 4-Methoxybenzyl Ester

Anisyl chloride (50.6 g.) was added to a stirred solution of 6-alpha-hydroxypenicillanic acid (71 g.) in N,N-dimethylformamide (540 ml.) containing triethylamine (57 g.). The mixture was stirred at room temperature for 17 hours and then partitioned between water (1 l.) and ethyl acetate (1 l.). The organic phase was separated, washed in turn with water (2×500 ml.), saturated sodium bicarbonate (500 ml.) and brine (500 ml.) and dried over magnesium sulfate. Evaporation of the solvent gave an oil which was chromatographed on silica eluting with petroleum ether (b.p. 60°-80° C.) to give 6-alpha-hydroxypenicillanic acid 4-methoxybenzyl ester (15 g., 13%) as an oil.

N.M.R. ($CDCl_3$) delta: 1.35 (s, 3H); 1.50 (s, 3H); 3.78 (s, 3H); 4.42 (s, 1H); 4.77 (d, 1H); 5.10 (s, 2H); 5.22 (d, 1H); 7.05 (q, 4H).

PREPARATION 3

6-beta-Hydroxypenicillanic Acid 2,2,2-Trichloroethyl Ester

A solution of sodium borohydride (0.23 g.) in 50% aqueous ethanol (350 ml.) was added with stirring to a solution of 6-oxopenicillanic acid 2,2,2-trichloroethyl ester (2.8 g.) in 50% aqueous ethanol (250 ml.) at 0° C. After 2 minutes the reaction mixture was acidified to pH 2 with 20% phosphoric acid (90 ml.) and extracted with dichloromethane (2×100 ml.). The combined organic extracts were washed with 5% aqueous sodium bicarbonate (100 ml.) and water (100 ml.), dried ($Na_2SO_4$) and evaporated to give an orange oil. Chromatography on silica eluting with a gradient of dichloromethane containing an increasing proportion of diethyl ether gave 6-beta-hydroxypenicillanic acid 2,2,2-trichloroethyl ester (0.54 g.).

N.M.R. ($CDCl_3$) delta: 1.59 (s, 3H); 1.70 (s, 3H); 4.61 (s, 1H); 4.81 (s, 2H); 5.21 (bs, changed to d, J=4 Hz by $D_2O$, 1H); 5.58 (d, J=4 Hz, 1H); also OH at 3.53 (bd, 1H).

I.R. (film): 1760-1780 $cm^{-1}$.

PREPARATION 4

6-beta-Hydroxypenicillanic Acid Pivaloyloxymethyl Ester

A solution of 6-aminopenicillanic acid pivaloyloxymethyl ester p-toluenesulfonic acid salt (4.0 g.) in dichloromethane (40 ml.) was added dropwise with stirring to a cooled solution of p-toluenesulfonic acid (2.0 g.) and sodium nitrite (8.8 g.) in a mixture of dichloromethane (360 ml.) and water (400 ml.). The mixture was stirred at 0° C. for 30 minutes and for a further 1 hour at room temperature. The organic layer was separated, dried ($Na_2SO_4$) and concentrated to a volume of 150 ml.

The solution was cooled in an ice bath and stirred while triphenylphosphine was added (2.17 g.) followed by the dropwise addition of a solution of sodium nitrite (2.71 g.) in trifluoroacetic acid (3.25 ml.) and dimethylsulfoxide (110 ml.). The mixture was stirred at 0° C. for a further 2 hours and then washed in turn with water, 5% aqueous sodium bicarbonate and water. The solution was dried (Na$_2$SO$_4$) and the solvent evaporated under vacuum. The crude 6-oxo product was immediately taken up in a mixture of methanol (62.5 ml.) and ethanol (62.5 ml.) and the solution was cooled in an ice bath and stirred while a solution of sodium borohydride (0.17 g.) in a mixture of water (62.5 ml.) and ethanol (62.5 ml.) was added. After 2½ minutes the mixture was acidified to pH 2 with 20% phosphoric acid and extracted with dichloromethane (2×100 ml.). The combined organic extracts were washed with 5% aqueous sodium bicarbonate and water and dried (Na$_2$SO$_4$), and the solvent evaporated under vacuum to yield the crude product which was purified by chromatography on silica eluting with a gradient of dichloromethane containing an increasing proportion of diethyl ether to give 6-beta-hydroxypenicillanic acid pivaloyloxymethyl ester (0.95 g.).

N.M.R. (CDCl$_3$) delta: 1.20 (s, 9H); 1.52 (s, 3H); 1.63 (s, 3H); 4.46 (s, 1H); 5.22 (m, or after D$_2$O exchange d, J=4 Hz, 1H); 5.69 (d, J=4 Hz, 2H); 5.83 (d, J=6 Hz, 1H); 5.87 (d, J=6 Hz, 1H).

I.R. (film): 1800 cm$^{-1}$ (beta-lactam carbonyl).

PREPARATION 5

6-alpha-Hydroxypenicillanic Acid 4-Nitrobenzyl Ester

4-Nitrobenzyl bromide (5.0 g.) was added to a stirred solution of 6-alpha-hydroxypenicillanic acid (5.0 g.) and triethylamine (2.3 g.) in N,N-dimethylformamide (50 ml.). The reaction mixture was stirred overnight at room temperature and water (100 ml.) and ethyl acetate (100 ml.) were added. The organic layer was separated, washed in turn with water, dilute sodium bicarbonate and brine, dried over MgSO$_4$ and evaporated to yield a red gum. Chromatography on silica eluting with a mixture of ethyl acetate and dichloromethane gave the product (2.52 g.).

N.M.R. (CDCl$_3$) delta: 1.41 (s, 3H); 1.55 (s, 3H); 4.52 (s, 1H); 4.80 (bs, 1H); 5.20–5.32 (m, 3H); 7.54 (d, J=8.5 Hz, 2H); 8.19 (d, J=8.5 Hz, 2H).

I claim:
1. A compound having the formula

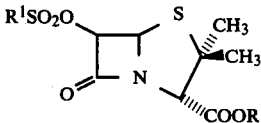

wherein R is H, a conventional penicillin carboxy protecting group or an ester forming residue readily hydrolyzable in vivo, and R$^1$ is a perfluoroalkyl or perchloroalkyl group having from 1 to 4 carbon atoms.

2. A compound according to claim 1 wherein said conventional penicillin carboxy protecting group is 4-methoxybenzyl, 4-nitrobenzyl benzhydryl, trichloroethyl or trimethylsilyl.

3. A compound according to claim 1 wherein said ester forming residue readily hydrolyzable in vivo is pivaloyloxymethyl.

4. A compound according to claims 2 or 3 wherein R$^1$ is trifluoromethyl or nonafluorobutyl.

5. A compound according to claim 1 wherein said compound is 6-alpha-trifluoromethylsulfonyloxypenicillanic acid benzhydryl ester, 6-alpha-trifluoromethylsulfonyloxypenicillanic acid 4-methoxybenzyl ester, 6-beta-trifluoromethylsulfonyloxypenicillanic acid 2,2,2-trichloroethyl ester, 6-alpha-trifluoromethylsulfonyloxypenicillanic acid, 6-beta-trifluoromethylsulfonyloxypenicillanic acid, 6-alpha-trifluoromethylsulfonyloxypenicillanic acid trimethylsilyl ester, 6-alpha-nonafluorobutylsulfonyloxypenicillanic acid benzhydryl ester, 6-beta-trifluoromethylsulfonyloxypenicillanic acid pivaloyloxymethyl ester or 6-alpha-trifluoromethylsulfonyloxypenicillanic acid 4-nitrobenzyl ester.

6. 6-alpha-trifluoromethylsulfonyloxypenicillanic acid benzhydryl ester.

* * * * *